United States Patent [19]
Castor

[11] Patent Number: 6,071,264
[45] Date of Patent: Jun. 6, 2000

[54] ANIMAL FEEDING/MEDICATING APPARATUS

[76] Inventor: Gerald Castor, 3250 W. Market St., Akron, Ohio 44333

[21] Appl. No.: 09/054,682

[22] Filed: Apr. 3, 1998

[51] Int. Cl.[7] .............................. A01K 9/00; A01K 7/00; A61M 5/178
[52] U.S. Cl. .............................. 604/183; 119/71; 119/72; 215/11.1
[58] Field of Search .............................. 119/51.5, 71, 72, 119/454, 464, 475, 833; 59/7, 8; 604/183, 184, 185–187, 181; 215/11.1–11.6

[56] References Cited

U.S. PATENT DOCUMENTS

| | | |
|---|---|---|
| 4,020,838 | 5/1977 | Phillips et al. . |
| 4,050,460 | 9/1977 | Magrath .................................. 128/223 |
| 4,257,354 | 3/1981 | Gillette et al. .......................... 119/72.5 |
| 4,301,934 | 11/1981 | Forestal .................................. 215/11 D |
| 4,620,505 | 11/1986 | Thomson et al. .......................... 119/71 |
| 4,773,898 | 9/1988 | Begouen .................................. 604/79 |
| 4,813,871 | 3/1989 | Friedman . |
| 4,925,042 | 5/1990 | Chong .................................. 215/11.1 |
| 4,969,564 | 11/1990 | Cohen et al. .......................... 215/11.1 |
| 4,973,248 | 11/1990 | Sigler . |
| 5,033,412 | 7/1991 | Brennan et al. .......................... 119/72 |
| 5,037,399 | 8/1991 | Reichert et al. . |
| 5,053,022 | 10/1991 | Bryant et al. . |
| 5,057,077 | 10/1991 | Turner et al. . |
| 5,139,488 | 8/1992 | Klein . |
| 5,188,610 | 2/1993 | Rains . |
| 5,318,539 | 6/1994 | O'Neil . |
| 5,524,576 | 6/1996 | Walther .................................. 119/51.01 |

*Primary Examiner*—Wynn Wood Coggins
*Assistant Examiner*—Jennifer R. Sadula
*Attorney, Agent, or Firm*—Oldham & Oldham Co., L.P.A.

[57] ABSTRACT

The invention is directed to an apparatus for the oral administration of a flowable material to an animal. The apparatus may be useable in artificial feeding or administration of medication to an animal, and in general includes a container to hold a predetermined amount of the liquid or flowable material to be administered. The container has a discharge opening through which the liquid is selectively discharged to a feeding tube selectively coupled to the discharge opening. The tube is in fluid tight relationship to receive liquid or flowable material discharged from the container, and has a predetermined length and a distal discharge end through which the material is transmitted. A nipple which can be associated with the tube is selectively positioned at a predetermined location relative to the distal end of the tube. The nipple is configured to limit the extent to which the tube can be inserted into the mouth of the animal and to facilitate proper administration of the material to the animal.

20 Claims, 2 Drawing Sheets

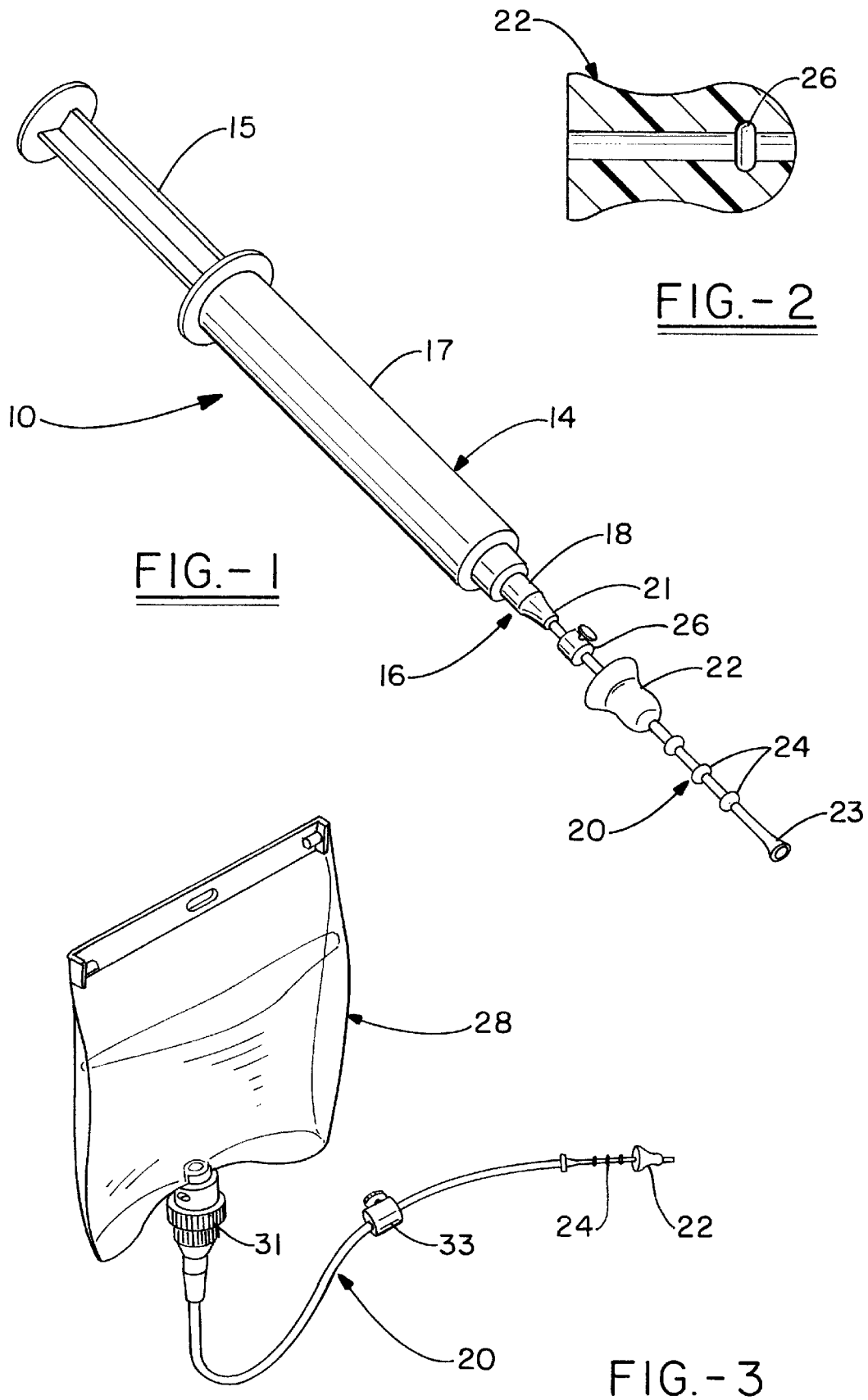

ANIMAL FEEDING/MEDICATING APPARATUS

BACKGROUND OF THE INVENTION

The present invention relates generally to an animal feeding and/or medicating apparatus. More specifically, the present invention relates to an apparatus which allows the amount of feeding or medicating formula to be measured and also allows for correct placement of the formula into the animal's digestive tract or mouth.

Many devices have been created to allow animal owners, or veterinarians to administer feeding or medicating solutions to animals orally. For example, there are known devices which are referred to as dose syringes which administer liquid medications in a spray form, but such devices cannot be used for other purposes such as to administer artificial feeding formulas. In many situations, a young or baby animal may require artificial feeding, such as if the animal is too weak, premature, sick or for other reasons. In some instances, flexible tubes have been employed which are inserted into the mouth, and in some cases into the esophagus for these purposes. Such devices are many times difficult to handle or may not allow the operator to accurately measure the amount of formula, solution or dose of medication being delivered or administered to the animal. Those devices also lack a means to correctly place the feeding tube into the mouth of the animal to ensure that the feeding or medicating formula is effectively utilized and not wasted. Further, when using those devices, complications such as ear infections have arisen after feeding or medicating when the formula has entered the ear canal. There is thus a need for an apparatus which allows the operator to monitor the amount of formula or other solution that is being administered to the animal.

Additionally, based upon the condition of the animal and the particular requirements for medicating or artificially feeding the animal, the oral administration of liquid solutions may vary for the most effective administration to the animal. No apparatus exists which allows an operator to effectively adjust the characteristics of the apparatus for the particular needs and application of food, medicine or other materials, therefore allowing the apparatus to be tailored for the particular application or animal. Proper placement of the formula or medication into the esophagus or mouth of the animal ensures that the formula or medication does not enter the ear canal or other inappropriate places and avoids waste of these materials.

SUMMARY OF THE INVENTION

The present invention allows an animal owner, veterinarian, or other operator to easily administer feeding or medicating formulas or solutions to animals orally. Further, the present invention allows for the formula to be put directly into the animals digestive tract if desired, so as to reduce the risk that the formula may enter the animal's nasal or ear cavities. For many applications, this inhibits infection in the animal's ear and also ensures that the formula is most effectively utilized. Alternatively, for other applications, the present invention allows for the formula to be placed into the animal's mouth, with or without the amount of formula administered to the animal being effectively monitored. The present invention allows adjustment of the apparatus for the particular application and use, whether for oral feeding of an animal using formula or other manufactured products for administration of medication or other purposes. In general, the invention is directed to an apparatus via oral administration which comprises a container used to hold a predetermined amount of flowable material to be administered to the animal. The container has a discharge opening through which the liquid is selectively discharged to the animal. A tube is selectively coupled to the discharge opening in sealed tight relationship to receive the liquid or other flowable material discharged from the container, the tube having a predetermined length and a distal discharge end. A nipple member is associated with the tube and positioned at a predetermined location relative to the distal end of the tube, the nipple member being configured to limit the extent the tube can be inserted into the mouth of the animal. Additionally the nipple member may be configured to simulate an animals natural feeding environment, and shaped as an arcuate body, a triangular body or in another desirable shape depending on the animal. The nipple may be removed from the tube to facilitate easier viewing of the placement of the distal end. In the preferred embodiment, the tube is flexible, and different diameter tubes may be used for feeding, medicating or other applications, or for a particular type or size of animal. Further in the preferred embodiment, the nipple associated with the tube is adjustable relative to the distal end of the tube, allowing the configuration to be tailored for a particular animal and/or application. The nipple may be selectively positioned in association with the tube to allow different nipples to be easily used with the apparatus, again tailoring the apparatus to the specific animal and/or application. Alternatively, the nipple may be integrally positioned with respect to the distal end of the tube for use with a particular type or size of animal or for a particular application. The formula container can be a common syringe, an infusion type feeding bag, a bottle, or any other suitable container, preferably with indicia to allow the operator to determine the amount of formula being administered to the animal.

It is an object of the present invention to provide a simple and effective apparatus which is easily adjusted for use and enables accurate measurement of a feeding and or medicating formula as it is being administered to an animal. This and other objects of the invention will become apparent upon a reading of the detailed description of preferred embodiments in conjunction with the drawings.

BRIEF DESCRIPTION OF THE DRAWINGS

FIG. 1 is a pictorial view of the preferred embodiment of the present invention.

FIG. 2 is a cross sectional view of a nipple of an alternative embodiment of the present invention.

FIG. 3 is a pictorial view illustrating an alternative embodiment of the invention.

DETAILED DESCRIPTION OF THE PREFERRED EMBODIMENTS

Figure 4:
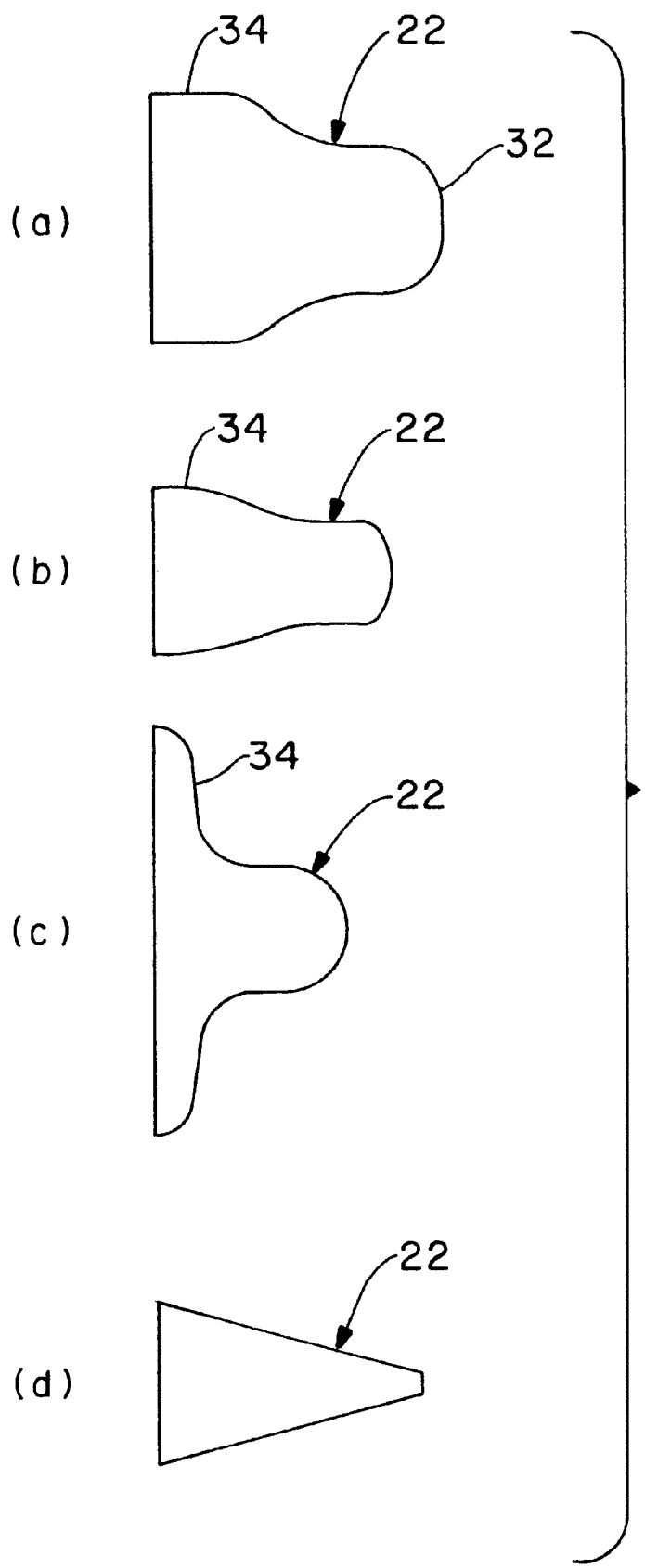
FIGS. 4a–4d show various embodiments of a nipple associated with the invention.

Reference will now be made in detail to the present preferred embodiments of the invention, examples of which are illustrated in the accompanying drawings. Whenever possible, the same reference numbers will be used throughout the drawings to refer to the same or like parts.

The oral administration of various flowable materials or liquids, such as milk, feeding formulas, medications, vitamins or dietary supplements, is many times necessary to ensure and maintain proper health in a variety of animals. Further, artificial feeding or supplementing may become necessary for weak or sickened animals, and particularly for newborn animals of various types. In some cases, a young or baby animal will not or cannot feed from its mother, or its mother is not available, necessitating artificial feeding to allow the animal to survive and thrive. The present invention provides an apparatus which facilitates artificial feeding or the administration of other liquids to an animal, while tailoring the apparatus for the particular application and animal with which it is used. The feeding apparatus in accordance with the present invention is generally shown at 10 in FIG. 1, and comprises a container 14, which in this embodiment is a barrel syringe, to which a feeding tube 20 is attached at the outlet port 16 of the syringe. Feeding tube 20 may be constructed from any medical grade material as is known in the art and can differ as needed for different applications. In many applications, tube 20 may be flexible, but also may be rigid over all or a portion of its length. The feeding tube 20 can be attached to the outlet port 16 by means of a friction fit over the outlet port 16 of the syringe 14 or can be attached by means of a luer lock 18 or another coupling. In the preferred embodiment, the coupling is convenient and may also comprise a snap on arrangement or a screw threaded engagement. The container 14 could therefore be a bottle or like container having a lid which could be replaced or used in coupling tube 20 thereto. For flexibility, the coupling of the feeding tube 20 to the container or syringe 14 may allow the length of the feeding tube 20 to be adjusted relative to syringe 14. The feeding tube 20 may for example extend into the body of the syringe 14, allowing a comfortable length for administering liquid from the syringe to an animal through the tube 20. In a preferred embodiment, the tube 20 has a predetermined length with respect to the outlet port 16 of the syringe 14. In this embodiment, the syringe 14 may include a plunger 15 at the posterior end of the assembly, which is pushed in by the user for selective administration of liquid materials inserted into the barrel 17 of syringe 14. In the preferred embodiment, no material is discharged from container 14 except selectively by the user, preventing waste, drippage, or spillage of the material. Material is preferably only discharged by user activation or by the animals sucking response. At the forward end of syringe 14, the hub of a luer lock fitting 18 is provided, which allows coupling of a corresponding luer lock fitting 21 provided in association with feeding tube 20. Slidably fitted around flexible feeding tube 20 is a nipple member 22. This nipple member 22 can be manufactured from any suitable medical grade material and in various different shapes and sizes in order to accommodate different sized animals or applications. The nipple member 22 can be shaped as a body part having arcuate portions to simulate the animals natural feeding environment, or may be triangular or in some other shape as desired. The softness, resiliency and texture of member 22 can also be modified accordingly. In some applications, the feeding tube 20 is designed to have a length and size to be inserted through the animal's mouth and into its esophagus or even further into the digestive tract of the animal. In such an application, the feeding tube 20 is designed to have the proper length and diameter to be accommodated by a particular animal, and it should be recognized that much variation would therefore exist in these parameters. Such applications may relate to artificially feeding the animal or allowing medication to be administered over a period of time in known quantities. In an embodiment where the apparatus is to be used in such an application, the distal end thereof may be provided with an optional fitting 23 to facilitate dispensing the liquid from the feeding tube 20 while not adversely affecting breathing through the throat of the animal. Alternatively, if the apparatus is to be used with the feeding tube 20 extending only into the mouth of the animal, the fitting 23 may be provided as a nipple or diaphragm member which will facilitate administration when the animal performs a suckling response. The fitting 23 may thus be of various types to accommodate a particular application or a particular animal, and may be constructed integrally with feeding tube 20 or as a separate member coupled with tube 20. The arrangement of the feeding tube 20 in conjunction with nipple member 22 and/or fitting 23 is preferably designed according to either a particular animal or delivery system. These components of the delivery system are preferably designed to provide a natural feel to the animal, and the softness, resiliency, shape, texture and other possible attributes of these components can facilitate transition back to a natural feeding environment for the animal. All these attributes of these components will vary for the particular animal, and these variations would be recognized by those skilled in the art and are contemplated and encompassed by the invention.

Forming the distal end of tube 20 with a fitting 23 or coupling such a fitting thereto also serves to function as a retaining collar for the nipple 22, such that it cannot be slid off tube 20 when in use. Alternatively, one or more retaining members or collars 24 may be provided in association with tube 20 to facilitate proper positioning of the nipple 22 as well as to retain the nipple 22 thereon. In the preferred embodiment, the retaining collars 24 may be molded directly into the feeding tube 20 but may also be separate members selectively positioned and secured with tube 20. Providing a plurality of retaining collars 24 at particular positions along feeding tube 20 may further facilitate positioning of nipple 22 at a predetermined and desired location. Although the retaining collars 24 will in general prevent nipple 22 from slipping off of tube 20, they may also be used in conjunction with nipple 22 for positioning thereof. As shown in FIG. 2, nipple 22 may be constructed to include a positioning mechanism 26, such as a groove formed to correspond to the outwardly extending retaining collars 24 associated with tube 20. In such an embodiment, as the nipple 22 is slid along the length of feeding tube 20, the forward end thereof will encounter a retaining collar 24. The nipple 22 as well as tube 20 and retaining collar 24 may be constructed of a slightly resilient material to allow the nipple to be urged over a retaining collar 24 by application of enough pressure to the rear end of nipple 22 by the user. The force which must be applied to accomplish this should be somewhat more than the force that could be applied to the nipple after insertion into the mouth or throat of the animal. It should then be recognized that nipple 22 could be moved forwardly until retaining collar 24 is positioned within retaining mechanism 26, to further facilitate retention of nipple 22 in this fixed position. Providing the plurality of collars 24 allows the position of nipple 22 to be selectively adjusted in precise increments to facilitate its use. Further in association with feeding tube 20, a tube clamp 26 may be provided at any position along the length of tube 20 to selectively open and close the tube for control of liquid administration to the animal.

FIG. 3 illustrates another embodiment of the present invention wherein the formula or liquid container is a transparent or translucent bag or bottle 28 such as is known and used in the art, that preferably has indicia on it to enable the operator to monitor the amount of formula that is being administered to the animal. The bag 28 is connected to the feeding tube 20 by means of a connector or adaptor 31. The feeding tube 20 may be attached to the adapter 31 by a friction fit, a luer lock connector, a screw thread connector or any other suitable means 31. The use of the bag 28 allows for larger amounts of formula to be administered as may be necessary for larger animals. On tube 20, there may also be provided a flow control mechanism 33 which allows the user to selectively control the amount of material dispensed from container 28 or the flow rate of material. The arrangement of the feeding tube and nipple configuration may be similar to that described with reference to FIG. 1.

Turning now to FIG. 4, several embodiments of preferred nipples 22 are shown. The nipples 22 are again designed for specific applications and animals, and a wide variety is thus contemplated to accommodate these differences. As merely examples, FIG. 4 shows several embodiments, wherein embodiment (a) is similar to that previously shown and includes a forward end 32 directed toward the distal end of feeding tube 20 for insertion into the animals mouth and/or throat. The body of the nipple 22 may thereafter be reduced slightly from a slightly enlarged forward portion, and thereafter expand into a small flange 34 at the rear portion thereof. In embodiment (b), the size of the nipple 22 has been significantly reduced as compared to embodiment (a), with a diameter which is only slightly larger than the diameter of the tube 20 with which nipple 22 is to be used. Similarly, the flange portion 34 of nipple 22 has a significantly reduced diameter. The nipple 22 of example (b) would be suitable for a newborn or baby animal as compared to a larger nipple 22 as shown in example (a). Further, for a particular application, it may be desired to insert the distal end of feeding tube 20 at a predetermined location relative to the physiology of the animal. Nipple 22 as shown in example (c) of FIG. 4 may be adapted to position itself at a predetermined location relative to the animal's mouth or throat opening, allowing the distal end of feeding tube 20 to then extend to a predetermined location relative to this position. To facilitate retention at the desired location, the flange portion 34 may have a significantly greater diameter. The nipple 22 may also be configured for a particular type of animal, such as shown in example (d), wherein nipple 22 is shaped to facilitate the feeding of ornithologic offspring. Such tips or nipples suitably constructed are applicable in all species. It should also be recognized that the examples shown in FIG. 4 are by no means representative of the additional types of nipples 22 which may be beneficially used in conjunction with the feeding tube 20, and the shape, size or other attributes of the nipple 22 may vary to accommodate a particular application or animal.

In use, the operator fills the formula container with the desired feeding or medicating solution to be administered to the animal. This can be done by drawing the formula into the syringe 14 or by filling the bag or bottle 28 with the desired amount of formula. The operator then places the apparatus, and more particularly the distal end of tube 20 and nipple 22, into the mouth of the animal making sure that the apparatus is placed properly. The operator may then expel the formula through the syringe as rapidly as necessary or appropriate for the application, or can allow the animal control the rate of administration of the formula by selection of an appropriate bag or bottle 28 as the formula container.

It should be recognized that the apparatus of the invention allows the configuration of container 14 or 28, feeding tube 20 and nipple 22 to be adjusted for a particular application or animal. The ability to vary the position of nipple 22 with respect to tube 20 and to vary the configuration of nipple 22 allows great adaptability to various particular applications with which the apparatus may be useful. It should also be understood that although the preferred embodiments described herein are representative of the invention, the invention is clearly open to variations in various details and embodiments. Persons of ordinary skill in the art would recognize such variations, and thus equivalent elements may be substituted for those specifically shown and described, or features may be used independently of other features in a desired embodiment, all without departing from the scope of the invention as defined in the independent claims.

I claim:

1. An apparatus for the oral administration of a flowable material to an animal or non-human species comprising, a container to hold a predetermined amount of a flowable material to be administered to an animal, said container having a discharge opening through which said flowable material is selectively discharged, a tube selectively coupled to said discharge opening in fluid tight relationship to receive material discharged from said container, said tube having a predetermined length and a distal discharge end, and a nipple member associated with said tube and positioned at a predetermined location relative to said distal end of said tube, said nipple member being configured to limit the extent said tube can be inserted into the mouth of said animal or non-human species.

2. The apparatus as recited in claim 1, wherein said container is a barrel syringe.

3. The apparatus as recited in claim 1, wherein said container is a liquid impermeable housing.

4. The apparatus as recited in claim 1, wherein said tube is flexible along its length.

5. The apparatus as recited in claim 1, wherein said tube is rigid over at least a portion of its length.

6. The apparatus as recited in claim 1, wherein said nipple member is moveably positioned in association with said tube, with the position of said nipple being selectively variable.

7. The apparatus as recited in claim 1, wherein said nipple member includes positioning mechanism associated therewith to facilitate positioning thereof at said predetermined location.

8. The apparatus as recited in claim 1, wherein said tube includes at least one retaining collar provided in association therewith which inhibits removal of said nipple member from said tube.

9. The apparatus as recited in claim 1, wherein said tube includes a plurality of positioning members at predetermined positions along the length of said tube.

10. The apparatus as recited in claim 1, wherein said nipple member has an aperture through which said tube is positioned, and a forward end having a first diameter as well as a rearward end having a second diameter.

11. The apparatus as recited in claim 10, wherein said first diameter is smaller than said second diameter.

12. The apparatus as recited in claim 1, wherein said nipple member is shaped to simulate an animals natural feeding environment when positioned in the mouth of said animal.

13. The apparatus as recited in claim 1, wherein said nipple member is formed having at least one arcuate portion.

14. The apparatus as recited in claim 1, wherein said nipple member is formed as having at least one triangularly shaped portion.

15. The apparatus as recited in claim 1, wherein said nipple member is formed of a material having a predetermined resiliency to simulate the natural feeding environment of an animal.

16. The apparatus as recited in claim 1, wherein said nipple member is formed as having a texture simulating the natural feeding environment of an animal.

17. The apparatus as recited in claim 1, wherein said tube is selectively coupled to said discharge opening by means of a luer lock coupling.

18. The apparatus as recited in claim 1, wherein said tube is selectively coupled to said discharge opening by a snap on coupling.

19. The apparatus as recited in claim 1, wherein said tube is selectively coupled to said discharge opening by a screw thread coupling.

20. The apparatus as recited in claim 1, wherein the tube diameter is constant.

* * * * *